United States Patent [19]

Narisada et al.

[11] Patent Number: 5,002,972
[45] Date of Patent: Mar. 26, 1991

[54] COMPOUND AND COMPOSITION OF SUBSTITUTED HEXENOIC ACID DERIVATIVES USEFUL FOR TREATING THROMBOXANE $A_2$ MEDIATED DISEASES

[75] Inventors: Masayuki Narisada, Osaka; Mitsuaki Ohtani; Fumihiko Watanabe, both of Nara; Takaharu Matsuura, Hyogo, all of Japan

[73] Assignee: Shionogi & Co., Ltd., Osaka, Japan

[21] Appl. No.: 476,545

[22] Filed: Feb. 7, 1990

[30] Foreign Application Priority Data

Feb. 20, 1989 [JP] Japan ................................. 1-40824

[51] Int. Cl.$^5$ ..................... A61K 31/18; C07C 311/14
[52] U.S. Cl. ..................... 514/604; 514/822; 514/826; 514/929; 564/84; 564/88; 564/89; 564/90; 564/93
[58] Field of Search ............... 514/381, 518, 604, 822, 514/826, 929; 564/84, 88, 89, 90, 93

[56] References Cited

U.S. PATENT DOCUMENTS 4,861,913 8/1989 Narisada et al. ................ 562/427
4,916,231 4/1990 Narisada et al. ................ 548/252

Primary Examiner—Stanley J. Friedman
Assistant Examiner—G. Hollinden
Attorney, Agent, or Firm—Wenderoth, Lind & Ponack

[57] ABSTRACT

Pharmaceutical compounds and compositions for injectable use in the treatment of thromboxane $A_2$ mediating diseases, comprising a pharmaceutical carrier and a pharmacologically effective amount of a compound of the formula:

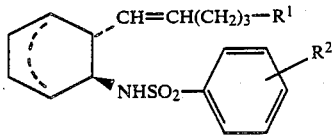

wherein $R^1$ is carboxyl or 5-tetrazolyl; $R^2$ is hydrogen, methyl, hydroxy, chloro, or bromo; or a pharmaceutically acceptable ester or salt thereof, together with one or more non-toxic pharmaceutically acceptable carriers; and methods for treating thromboxane $A_2$ mediating diseases.

6 Claims, No Drawings

COMPOUND AND COMPOSITION OF SUBSTITUTED HEXENOIC ACID DERIVATIVES USEFUL FOR TREATING THROMBOXANE $A_2$ MEDIATED DISEASES

BACKGROUND OF THE INVENTION

1. Field of the Invention

This invention relates to pharmaceutical preparations and methods for treating the thromboxane $A_2$ mediating diseases as the compounds of this invention have potent thromboxane $A_2$ ($TXA_2$) receptor antagonistic action. In more detail, this invention relates to the pharmaceutical preparations and methods for treating the thromboxane $A_2$ mediating diseases using phenylsulfonylaminobicyclo [2.2.1]heptylhexenoic acid derivatives or pharmaceutically acceptable esters and salts thereof as an effective ingredient. The said pharmaceutical preparations are useful as anti-thrombosis, anti-vasoconstrictor, antibronchoconstrictor and so forth.

2. Prior Art

Previously, the inventors found that numbers of bicyclicsulfonamide derivatives have potent $TXA_2$ receptor antagonistic activity and many of them are disclosed in U.S. Pat. No. 4,861,913.

Among them, the bicyclo[2.2.1]heptane-type derivatives appear promising because of their quite high pharmacological activities and low toxicities. These compounds show excellent efficacies in an administration where the blood level is gently elevated, such as oral adminstration. It has been recognized, however, that they show the transient $TXA_2$ receptor agonistic actions (partial agonistic actions) just after the administration, if they are used in an administration which causes sudden, high elevation of the blood level, such as one-shot intravenous infusion. The adverse reactions like this make those compounds undesirable for the injectable purpose.

It is desired to develop such $TXA_2$ receptor antagonists which can be administrated intraveneously.

SUMMARY OF THE INVENTION

This invention provides pharmaceutical preparations for injectable use in the treatment of thromboxane $A_2$ mediating diseases in mammals containing a pharmacologically effective amount of at least a compound of the formula:

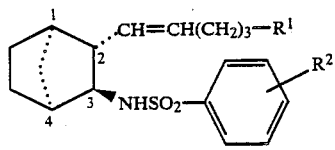

wherein $R^1$ is carboxyl or 5-tetrazolyl; $R^2$ is hydrogen, methyl, hydroxy, chloro, or bromo; or a pharmaceutically acceptable ester or salt thereof as an effective ingredient, together with one or more non-toxic pharmaceutically acceptable carriers and the method for treating the thromboxane $A_2$ mediating diseases.

DETAILED DESCRIPTION OF PREFERRED EMBODIMENTS

The inventors have studied hard to solve the problem and have prepared many compounds. They found that the substituted hexenoic acids of the formula (I):

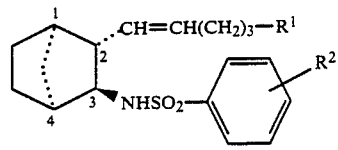

wherein $R^1$ is carboxyl or 5-tetrazolyl; $R^2$ is hydrogen, methyl, hydroxy, chloro, or bromo or a pharamceutically acceptable ester or salt thereof meet the purpose of this invention. This invention was based on these findings.

As apparently understood from the formula (I), the compounds ($R^1$=carboxyl) of this invention fall within the scope of the invention previously patented as U.S. Pat. No. 4,861,913 (JP-A-63-139161). However, such substituted or unsubstituted phenylsulfonylaminobicyclo[2.2.1]heptylhexenoic acid derivatives as this invention provides are not specifically disclosed at all in the said patent, which merely discloses in its body that 5-hexenoic acid residues can be the substituents at the 2-position. Instead, compounds having mostly heptenoic acid residues at the 2-position are actually provided in the working examples of the application.

The compounds ($R^1$=tetrazolyl) of this invention are disclosed in U.S. Application Ser. No. 07/377,409, filed July 10,1989 (now U.S. Pat. No. 4,916,231).

The substituted or unsubstituted phenylsulfonylaminobicyclo[2.2.1]heptylheptenoic acids are recognized closest in structure to the subject compounds of this invention, among all the compounds of examples in the above-said application. The compounds of this invention are quite similar to those compounds and differ in structure due to lack of only one methylene group. Therefore, no one has been able to expect that such a little difference in structure provides so much difference in biological activity. As clearly shown by the formula, the compounds of this invention are the carboxylic acids and tetrazoles, so their pharmaceutically acceptable esters and salts which can be expected by persons skilled in the art are included in the scope of this invention.

In this specification, compounds of this invention are represented by the formula (I) of an absolute configuration for the convenience' sake, but are intended to include their enantiomers or the mixtures. The compounds having an absolute configuration shown by the formula (I) have the most potent activity and are preferable for the purpose of this invention. However, it is not a matter of importance to manufacture them with a high optical purity for the purpose of this invention because the asymmetric synthesis is costly and they, even if are optically impure, can show high activities at a very small dosage. Accordingly, in the following parts of this specification, those are generally called simply as the compounds of this invention.

The pharmacological effects of the compounds of this invention seem to be especially characterized by the hexenoic acid residues at the 2-position. Therefore, the substitutent such as methyl, hydroxy, chloro, or bromo on the phenyl of phenylsulfonylamino group which is the other side chain may be attached to either 2-, 3-, or 4-position. According to the inventors' study, those having phenyl unsubstituted or substituted with methyl, hydroxy, chloro, or bromo at 4-position are especially desirable for their major activities. The hydroxy may be esterified with acetyl or the like.

The compounds ($R^1$=carboxyl) of this invention can form esters as illustrated below.

Representative examples of the carboxyl-protecting ester are an ester with alkyl group having 1 to 8 carbon atoms (e.g., methyl, methoxymethyl, ethyl, ethoxymethyl, iodoethyl, propyl, isopropyl, butyl, isobutyl, ethoxyethyl, methylthioethyl, methanesulfonylethyl, trichloroethyl, tert-butyl ester), an ester with alkenyl group having 3 to 8 carbon atoms (e.g., propenyl, allyl, prenyl, hexenyl, phenylpropenyl, dimethylhexenyl ester), an ester with aralkyl group having 7 to 19 carbon atoms (e.g., benzyl, methylbenzyl, dimethylbenzyl, methoxybenzyl, ethoxybenzyl, nitrobenzyl, aminobenzyl, diphenylmethyl, phenylethyl, trityl, di-tert-butylhydroxybenzyl, phthalidiyl, phenacyl ester), an ester with aryl group having 6 ot 12 carbon atoms (e.g., phenyl, tolyl, diisopropylphenyl, xylyl, trichlorophenyl, pentachlorophenyl, indanyl ester), an ester with an N-hydroxyamino compound having 1 to 12 carbon atoms (e.g., ester with acetoxyme, acetophenonoxime, acetaldoxime, N-hydroxysuccinimide, N-hydroxyphthalimide), an ester with hydrocarbon-silyl group having 3 to 12 carbon atoms (e.g., trimethylsilyl, dimethylmethoxysilyl, tert-butyldimethylsilyl ester), an ester with hydrocarbon-stannyl group having 3 to 12 carbon atoms (e.g., trimethylstannyl ester), etc.

Representative examples of the pharmacologically active ester are an ester with 1-oxygen-substituted alkyl group having 2 to 15 carbon atoms such as straight, branched, cyclic or partially cyclic alkanoyloxyalkyl (e.g., acetoxymethyl, acetoxyethyl, propionyloxymethyl, pivaloyloxymethyl, pivaloyloxyethyl, cyclohexanacetoxyethyl, cyclohexanecarbonyloxycyclohexylmethyl ester), ester with alkoxycarbonyloxyalkyl having 3 to 15 carbon atoms (e.g., ethoxycarbonyloxyethyl, isopropoxycarbonyloxyethyl, isopropoxycarbonyloxypropyl, tert-butoxycarbonyloxyethyl, isopentyloxycarbonyloxypropyl, cyclohexyloxycarbonyloxyethyl, cyclohexylmethoxycarbonyloxyethyl, bornyloxycarbonyloxyisopropyl ester), an ester with alkoxyalkyl having 2 to 8 carbon atoms (e.g., methoxymethyl, methoxyethyl ester), an ester with 2-oxacycloalkyl having 4 to 8 carbon atoms (e.g., tetrahydropyranyl, tetrahydrofuranyl ester), an ester with substituted aralkyl having 8 to 12 carbon atoms (e.g., phenacyl, phthalidyl ester), an ester with aryl having 6 to 12 carbon atoms (e.g., phenyl, xylyl, indanyl ester), an ester with alkenyl having 2 to 12 carbon atoms (e.g., allyl ester), etc. These ester residue may further be optionally substituted.

When the pharmaceutical preparations are formulated from the compounds of this invention, the ester may be selected among the above mentioned groups to suit the desired purpose. The lower alkyl esters, especially, methyl ester is preferable.

When the phenyl is substituted by hydroxy, it may be esterified with an alkanoyl (e.g., acetyl or the like).

The compounds of this invention form the salts with alkali metal (e.g., lithium, sodium, potassium, or the like), with alkaline earth metal (e.g., calcium, magnesium, or the like), with organic base (e.g., triethylamine, 2-aminobutane, tert-butylamine, diisopropylethylamine, n-butylmethylamine, n-butyldimethylamine, tri-n-butylamine, dicyclohexylamine, N-isopropylcyclohexylamine, furfurylamine, benzylamine, methylbenzylamine dibenzylamine N, N-dimethylbenzylamine, 2-chlorobenzylamine, 4-methoxybenzylamine, 1-naphthylmethylamine, diphenylbenzylamine, triphenylamine, 1-naphthylamine, 1-aminoanthracene, 2-aminoantracene, dehydroabiethylamine, N-methylmorpholine, pyridine, or the like), with amino acid (e.g., lysine, arginine, histidine, or the like), or the like. Especially, the salt with sodium, calcium, or lysine is preferable.

The representative compounds of this invention are described as follows:

(1) (1R,2R,3S,4S)-(5Z)-6-(3-phenylsulfonylaminobicyclo[2.2.1]hept-2-yl)-5-hexenoic acid (Ia-b), (2) (1R,2R,3S,4S)-(5Z)-6-[3-(o-tolylsulfonylamino)bicyclo[2.2.1]hept-2-yl]-5-hexenoic acid, (3) (1R,2R,3S,4S)-(5Z)-6-[3-(m-tolylsulfonylamino)bicyclo[2.2.1]hept-2-yl]-5-hexenoic acid, (4) (1R,2R,3S,4S)-(5Z)-6-[3-(p-tolylsulfonylamino)bicyclo[2.2.1]hept-2-yl]-5-hexenoic acid (Ib-b), (5) (1R,2R,3S,4S)-(5Z)-6-[3-(2-hydroxyphenylsulfonylaminobicyclo[2.2.1]hept-2-yl]-5-hexenoic acid, (6) (1R,2R,3S,4S)-(5Z)-6-[3-(3-hydroxyphenylsulfonylaminobicyclo[2.2.1]hept-2-yl]-5-hexenoic acid, (7) (1R,2R,3S,4S)-(5Z)-6-[3-(4-hydroxyphenylsulfonylaminobicyclo[2.2.1]hept-2-yl]-5-hexenoic acid (Ic-b), (8) (1R,2R,3S,4S)-(5Z)-6-[3-(2-bromophenylsulfonylaminobicyclo[2.2.1]hept-2-yl]-5-hexenoic acid, (9) (1R,2R,3S,4S)-(5Z)-6-[3-(3-bromophenylsulfonylaminobicyclo[2.2.1]hept-2-yl]-5-hexenoic acid,

(10) (1R,2R,3S,4S)-5Z)-6-[3-(4-bromophenylsulfonylaminobicyclo[2.2.1]hept-2-yl]-5-hexenoic acid (Id-b),

(11) (1R,2R,3S,4S)-(5Z)-6-[3-(2-chlorophenylsulfonylaminobicyclo[2.2.1]hept-2-yl]-5-hexenoic acid,

(12) (1R,2R,3S,4S)-(5Z)-6-[3-(3-chlorophenylsulfonylaminobicyclo[2.2.1]hept-2-yl]-5-hexenoic acid,

(13) (1R,2R,3S,4S)-(5Z)-6-[3-(4-chlorophenylsulfonylaminobicyclo[2.2.1]hept-2-yl]-5-hexenoic acid (Ie-b),

(14) (1R,2R,3S,4S)-3-phenylsulfonylamino-2-[(1Z)-5-(5-tetrazolyl)-1-pentenyl]bicyclo[2.2.1]heptane (If-b),

(15) (1R,2R,3S,4S)-3-(2-bromophenylsulfonylamino)-2-[(1Z)-5-(5-tetrazolyl)-1-pentenyl]bicyclo[2.2.1]heptane,

(16) (1R,2R,3S,4S)-3-(3-bromophenylsulfonylamino)-2-[(1Z)-5-(5-tetrazolyl)-1-pentenyl]bicyclo[2.2.1]heptane, and

(17) (1R,2R,3S,4S)-3-(4-bromophenylsulfonylamino)-2-[(1Z)-5-(5-tetrazolyl)-1-pentenyl]bicyclo[2.2.1]heptane (Ig-b), and a pharmaceutically acceptable ester or salt thereof.

The compounds of this invention can be prepared by reacting the compound of the formula (II):

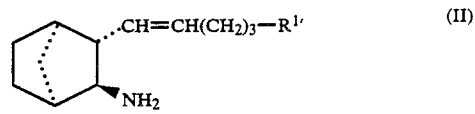

wherein $R^{1'}$ is COO-carboxyl protecting group or tetrazolyl, with the compound of the formula:

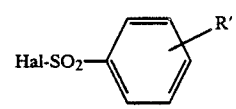

wherein R' is hydrogen, methyl, acetoxy, chloro, or bromo; Hal is halogen, and, optionally followed by deprotection, active ester formation, and/or salt formation.

The sulfonamide formation can be carried out in the usual manner, e.g., the manner disclosed in U.S. Pat. No. 4,861,913.

The deprotection can be carried out by the following usual manners, for example:

(1) the deprotection of carboxyl protecting group is generally carried out in the presence of an acid or a base in an inert solvent. In some special cases, for instance, the treatment with metal and acid may be applied to the deprotection of trichloroacethyl ester; and photo-irradiation to that of phenacyl ester, (2) aralkyl of the carboxyl protecting group can be deprotected by treating with an acid such as mineral acid, Lewis acid (e.g., aluminum chloride, stannous chloride, titanium chloride), sulfonic acid (e.g., benzenesulfonic acid, methanesulfonic acid, trifluoromethanesulfonic acid), strong acidity carboxylic acid (e.g., trifluoroacetic acid), if required, in the presence of a cationic scavenger such as anisole, benzenethiol, or the like, (3) tert-alkyl, cyclopropylmethyl, 2-alkenyl, aralkyl, sulfonylethyl, or the like of the carboxyl protecting group can be deprotected by treating with an acid such as mineral acid, Lewis acid (e.g., aluminum chloride, stannous chloride, titanium chloride), sulfonic acid (e.g., benzenesulfonic acid, methanesulfonic acid, trifluoromethanesulfonic acid), strong acidity carboxylic acid (e.g., trifluoroacetic acid), if required, in the presence of a cationic scavenger such as anisole, benzenethiol, or the like, (4) 2-alkenyl of the carboxyl protecting group can be deprotected by treating with triarylphoshine-palladium complex, (5) phenacyl, 2-alkenyl, hydroxyaralkyl of the carboxyl protecting group can be deprotected by treating with a base or nucleophilic reagent, and (6) other equivalent methods for deprotecting the carboxyl protecting group.

The esterification can be carried out by the following usual manner, for example:

(1) condensation of the carboxylic acid by dehydration with alcohol or phenol derivatives which form the desired ester in the presence of dicyclohexylcarbodiimide, (2) reacting the acid chloride with alcohol or phenol derivatives which form the desired ester in the presence of a base such as triethylamine, dimethylaniline, pyridine, sodium hydroxide, or the like, (3) reacting the carboxylic acid with alcohol, the corresponding alkene, or phenol derivatives which may form the desirable ester in the presence of acidic catalyst such as dry hydrocloric acid, conc. sulfonic acid, and (4) reacting the salt of carboxylic acid with alkyl halides which may form the desirable ester.

The salts of the carboxylic acid can be prepared in a conventional manner, for example, by reacting the carboxylic acid in a solvent with a theoretical amount of an suitable base such as an alkali metal or alkaline earth metal hydroxide or carbonate, ammonium hydroxide, ammonia, or an organic amine. The salts can be isolated by freeze-drying or, if it is sufficiently insoluble to the solvent, may be isolated by filtration after removing a part of solvent.

The most desirable compounds of this invention are the optically active compounds of the formula:

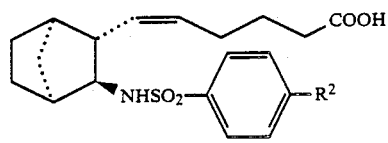

wherein $R^2$ is hydrogen, methyl, hydroxy, chloro, or bromo or pharmaceutically acceptable esters or salts thereof.

The compounds of the formula (II) can be easily prepared from the 3-substituted amino-2-bicyclo [2.2.1]heptylcarboxylic acid derivatives as follows.

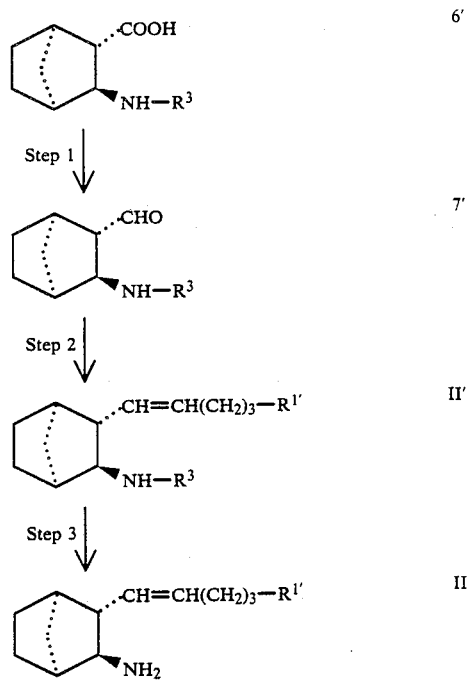

In the reaction scheme, $R^{1'}$ is COO-carboxyl protecting group or tetrazolyl and $R^3$ is amino protecting group.

Step 1

In this step, the carboxylic acid 6' is reduced to the aldehyde 7'.

This step can be carried out according to the method discribed in U.S. Pat. No. 4,861,913. As another method, this step can be achieved by transformation of carboxylic acid into an acid halide such as acid chloride followed by reduction of the resulting compound with metal hydride such as sodium borohydride.

Step 2

In this step, an ylide is condensed to the compound 7' to give the compound II'.

This step can be carried out according to an usual method of Wittig reaction.

The ylide used in this step can be prepared by the treatment of triphenyl [4-(5-tetrazolyl)butyl]phosponium bromide [J. Med. Chem., 22, 1340, (1979)] or 4-carboxylbutyltriphenylphosphonium bromide with a base (e.g., sodium hydroxide, n-butyl lithium, potassium tert-butoxide, sodium dymsyl, potassium dymsyl).

The reaction is carried out in a solvent such as ether (e.g., diethyl ether, tetrahydrofuran), n-hexane, dimethyl sulfoxide, or the like under heating or at room temperature for several hours.

The protection of carboxylic acid and the removal of amino protecting group in Step 3 can be carried out by the method described in U.S. Pat. No. 4,861,913. By the Wittig reaction in Step 2, compounds of Z-isomer is prepared in high yield. Trifluoroacetic acid salt of amine II prepared first in Step 3 may be applied to the next reaction.

The phenylsulfonyl residues may be used in place of the amino protecting group at 3-position.

The term "carboxyl protecting group" means all the aforementioned carboxyl protecting ester residue usually used in this field, including, for example, lower alkyl (e.g., methyl, ethyl, tert-butyl, or the like), and aralkyl (e.g., benzyl, 4-methoxybenzyl, triphenylmethyl, diphenylmethyl, or the like).

The term "amino protecting group" ($R^3$) means all the ordinary protecting groups, including, for example, alkoxycarbonyl (e.g., tert-butoxycarbonyl), aralkoxycarbonyl (e.g., benzyloxycarbonyl, diphenylmethoxycarbonyl), lower alkanoyl (e.g., formyl, acetyl) and the like.

The term "halide" includes fluoride, chloride, bromide, and iodide.

EFFECT OF THE INVENTION

Since the compounds of the present invention have a potent antagonistic activity against thromboxane $A_2$ receptor, they are useful for prevention and treatment of thromboxane $A_2$ mediating diseases such as bronchial asthma, inflammation, hypertension, thrombosis, apoplexy, myocardial infarction, cerebral infarction, or the like. Practically, showing no partial agonistic activity as shown in the following experimental, the compounds are especially suitable for an injection use. Moreover, having a superior stability and absorbability, the compounds of this invention may be formulated, if required, into oral form, suppository, or the like.

For the oral administration, they are normally formulated into conventional preparation form such as solid preparations (e.g., tablets, powders, capsules, granules) or liquid preparations (e.g., aqueous dispersion, oily suspension, syrups, elixirs). For the parenteral administration, they can be injected in a form of aqueous solutions or oily dispersions. Excipients, binding agent, lubricants, solvents, solubilizers, emulsifiers, dispersants, and the like may be used in formulating the above preparations. Other additives such as preservatives and stabilizing agents may be further added thereto.

The dosage of the compounds (I) of this invention varies with the dosage form, age, body weight, symptom of the patient, or the like but usually ranges from about 0.01 to 50 mg/kg daily, preferably, 0.05 mg to 10 mg/kg daily for oral administration and 0.001 mg/kg to 5 mg/kg daily, preferably, 0.005 mg/kg to 1 mg/kg daily for parenteral administration on a regimen in a single dose or 2 to 5 divided doses.

In this specification, 5-tetrazolyl means 5-1H-tetrazolyl or 5-2H-tetrazoly or their mixture.

Practical and presently preferred embodiments for this invention are shown in the following Examples, but it should be understood that these examples are given only for the illustrative purposes and do not limit the present invention thereto.

All the compounds prepared or used in examples and experiments are optically active compounds which have the absolute configurations shown by the formulas. This is intended to prove clearly the pharmacological effect of the subject compounds but not to exclued their enentiomers from the scope of this invention.

PREPARATION OF INTERMEDIATE 1

(1) Preparation of (1S,2R,3S,4R)-bicyclo[2.2.1]hept-5-en-2, 3-dicarboxylic acid 2-(benzyl D-mandelate) ester 2

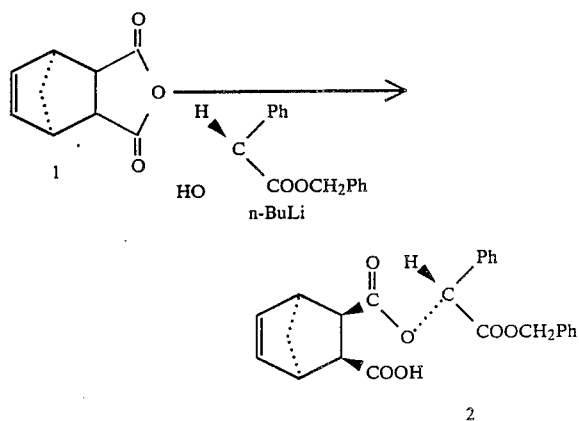

In a nitrogen atmosphere, a solution of benzyl D-mandelate (5.33 g (22.0 mmol)) in 50 ml of tetrahydrofuran (THF) is cooled to −78° C., then 13.13 ml (21.0 mmol) of 1.6M solution of n-butyllithium in hexane is added dropwise and the mixture is stirred for 15 minutes. To the reaction mixture is added a solution of 3.32 g (20.0 mmol) of bicyclo [2.2.1]hept-5-en-2-endo, 3-endo-dicarboxylic anhydride 1 in 20 ml of THF and the resulting mixture is stirred for an hour at −78° C. The reaction mixture is acidified with 2N hydrochloric acid and the product is extracted with ethyl acetate. The organic layer is washed with water and an aqueous solution of sodium chloride and concentrated to give 9.33 g of the crude product 2 which is purified by column chromatography on silica gel (toluene - ethyl acetate).

IR(film)$\nu$ max: 3600−2400, 1748, 1710, 1498, 1456, 1342, 1257, 1208, 1165, 1084, 1072, 912, 732, 696 cm$^{-1}$.

(2) Preparation of (1R,2R,3S,4S)-bicyclo[2.2.1]heptan-2,3-dicarboxylic acid 2-(D-mandelic acid) ester 3a

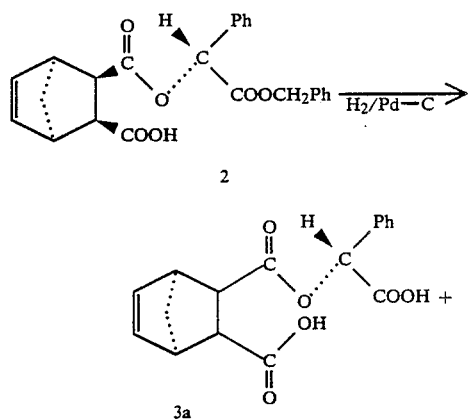

-continued

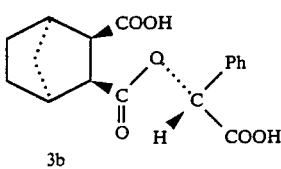

To a solution of 4.06 g (10.0 mmol) of crude product 2 in 30 ml of methanol is added 0.4 g of 10% palladium-carbon and the mixture is stirred in a hydrogen atmosphere under ordinary pressure at room temperature for 1.5 hours. The reaction mixture is filtered to remove the catalyst and the filtrate is concentrated. The residue is partitioned between ethyl acetate and 5% aqueous solution of sodium hydrogencarbonate and the aqueous layer is separated. The organic layer is extracted with water. The aqueous layers are collected and washed with ethyl acetate. After acidification with 2N hydrochloric acid the mixture is extracted with ethyl acetate. The organic layer is washed with an aqueous solution of sodium chloride and concentrated to give 3.14 g of the crude product 3a in 99% yield from acid anhydride. Compound 3a: Compound 3b=86:14 (Determined by HPLC).

The desired compound 3a is isolated by recrystallization from ethyl acetate. (2.05 g, yield 64%).

Mp. 164°–166° C.

[α]$_D$= −117.1±0.8° (MeOH, c=1.934, 25° C.).

(3) Preparation of (1R, 2S, 3S, 4S)-2-methoxycarbonyl-3-carboxybicyclo[2.2.1]heptane 4.

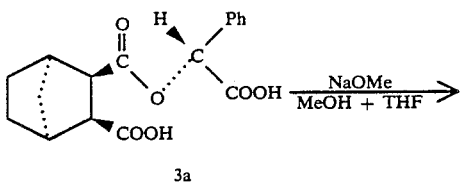

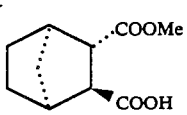

In a nitrogen atmosphere, a mixture of 5.51 g (17.3 mmol) of compound 3a, 40 ml of THF, 50 ml of methanol, and 22.0 ml (44.0 mmol) of sodium methoxide (2M solution in methanol) is refluxed for 4 hours. To the reaction mixture is added 2N hydrochloric acid and the mixture is extracted with ethyl acetate. The organic layer is washed with water and a saturated aqueous solution of sodium chloride, and concentrated. The residue is dissolved in dichloromethane and washed three times with water. The organic layer is concentrated to give 3.22 g of the desired compound 4 in 94% yield.

Mp. 59°–60° C.

[α]$_D$= +38.4±0.4° (MeOH, c=2.002, 25° C.).

(4) Preparation of (1R, 2S, 3S, 4S)-methyl 3-benzyloxycarbonylaminobicyclo[2.2.1]heptan-2-carboxylate 5

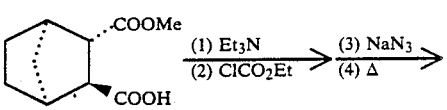

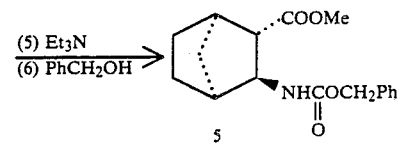

In a nitrogen atmosphere, a solution of 2.80 g (14.1 mmol) of the compound 4 in 24 ml of acetone is cooled to 0° C. and 2.54 ml (18.3 mmol) of triethylamine and 1.75 ml (18.3 mmol) of ethyl chlorocarbonate are added thereto. Then, colorless solids are precipitated immediately. The mixture is stirred for 15 minutes and a solution of 2.75 g (42.3 mmol) of sodium azide in 8 ml of water is added. The mixture is stirred under ice-cooling and acidified with 2N hydrochloric acid. The resulting mixture is extracted with ethyl acetate and the organic layer is washed with water and then with an aqueous solution of sodium chloride and concentrated. Benzene is added to the residue and concentrated again in order to remove ethyl acetate completely.

The resulting oil is dissolved in 20 ml of benzene and the mixture is heated to 80° C. to perform thermal rearrangement. When the evolution of nitrogen gas has ceased, 2.54 ml (18.3 mmol) of triethylamine and 1.75 ml (16.9 mmol) of benzyl alcohol are added and the resulting mixture is refluxed for 1.5 hours. After the reaction is finished, 2N hydrochloric acid is added to the reaction mixture which is then extracted with ethyl acetate. The organic layer is washed with water, and then with aqueous solution of sodium chloride and concentrated. The crude product is purified by column chromatography on silica gel and recrystallized to give 3.03 g of the compound 5 in 71% yield.

Mp.: 61°–62° C.

[α]$_D$= +40.1±0.4° (CHCl$_3$, c=2.006, 25° C.).

(5) Preparation of (1R, 2S, 3S, 4S)-3-benzyloxycarbonylaminobicyclo[2.2.1]heptan-2-carboxylic acid 6

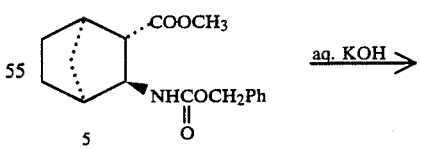

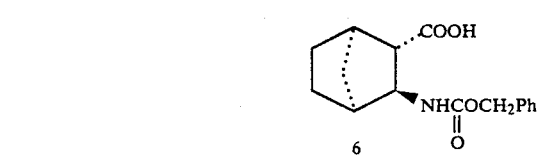

To a solution of 15.25 g (50.3 mmol) of the starting material 5 in 200 ml of methanol is added 100 ml (2×50.3 mmol) of 1N potassium hydroxide in a nitrogen atmosphere and the mixture is stirred for 2.5 hours at room temperature. The reaction mixture is poured into water and then acidified with 2N hydrochloric acid in the presence of ethyl acetate. The organic layer is washed with a saturated aqueous solution of sodium chloride, dried over magnesium sulfate, and concentrated under reduced pressure. The residue is recrystallized from n-hexane-ethyl acetate to give 14.10 g of the desired compound 6 in 96.9% yield.

Mp. 104.5°–106.5° C.

Anal. Calcd. (%) for $C_{16}H_{19}NO_4=289.33$: C, 66.42; H, 6.62; N, 4.84; Found (%): C, 66.48; H, 6.61; N, 4.80.

$[\alpha]_D= +20.8\pm0.6°$ (c=1.010, CHCl$_3$, 23° C.).

IR(CHCl$_3$)$\nu$ max: 3440, 2960, 2880, 2720, 1745, 1705, 1670, 1515 cm$^{-1}$.

NMR(CDCl$_3$)$\delta$ ppm: 1.17~1.82(m. 6H), 2.15(br.s, 1H), 2.43(br.s, 1H), 2.75~2.85(m, 1H), 3.83~3.93(m, 1H), 5.13(ABq, Apart, J=12.0, 1H), 5.18(ABq, Bpart, J=12.0Hz, 1H), 5.29(br.s, 1H), 7.38(br.s, 5H).

(6) (1R, 2S, 3S, 4S)-3-benzyloxycarbonylaminobicyclo[2.2.1]-heptan-2-carbaldehyde 7

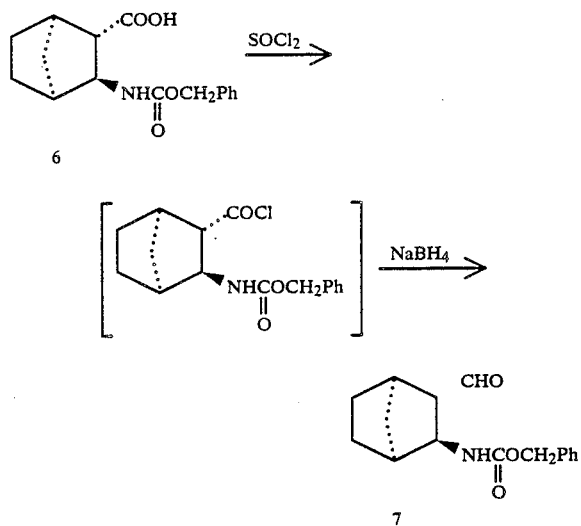

To a solution of 6.0 g (20.74 mmol) of carboxylic acid 6 in 100 ml of dry benzene are added 7.48 ml (5×20.74 mmol) of thionyl chloride and then 300 μl of pyridine and the mixture is refluxed for an hour. The reaction mixture is concentrated under reduced pressure and 30 ml of dry benzene is added thereto and the resulting mixture is concentrated under reduced pressure again to give the intermediate, acid chloride, quantitatively.

IR(film)$\nu$ max: 3285, 1782, 1692, 1515, 1261 cm$^{-1}$.

In a nitrogen atmosphere, 628 mg (0.8×20.74 mmol) of sodium borohydride is added to 36 ml of dry dimethylformamide and then 54 ml of dry tetrahydrofuran is added thereto to prepare a homogeneous solution, which is cooled to −70° C. to give a solid. Two minutes later, the mixture is warmed to 0° C. and then 2 minutes later the resulting paste is cooled to −70° C. To the mixture is added a solution of 20.74 mmol of the above prepared acid chloride in 12 ml of dry tetrahydrofuran over a minute.

The resulting mixture is stirred vigorously for 2 minutes and 40 ml of ethyl vinyl ether is added thereto. The mixture is poured into an ice-cold mixture of 20 ml of 2N hydrochloric acid and 80 ml of n-propionic acid under stirring vigorously. Further, 200 ml of saturated aqueous solution of sodium chloride and 100 ml of ethyl acetate are added and the resulting mixture is stirred for 2 minutes. The organic layer is separated and washed with a saturated aqueous solution of sodium chloride, 1N sodium hydroxide, and a saturated aqueous solution of sodium chloride again, successively, dried over magnesium sulfate, and concentrated under reduced pressure to give 4.23 g of the desired aldehyde 7 as an oil in 74.6% yield from the compound 6.

NMR(CDCl$_3$)$\delta$ppm: 1.10~1.80(m, 6H), 1.88~2.05(m, 1H), 2.40~2.60(m, 2H), 4.15~4.26(m, 1H), 4.80~5.16(m, 1H), 5.10(s, 2H), 7.36(s, 5H), 9.78(s, 1H).

(7) Preparation of (1R, 2R, 3S, 4S)-(5Z)-methyl 6-(3-benzyloxycarbonylaminobicyclo[2.2.1]hept-2-yl)-5-hexenoate 8a

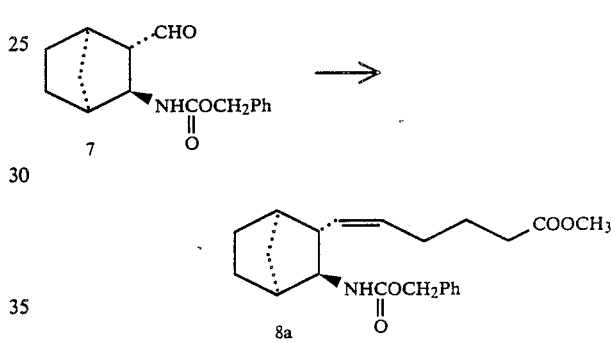

To a stirring suspension of 9.5 g (3×7.13 mmol) of 4-carboxybutyltriphenylphosphonium bromide in 90 ml of tetrahydrofuran under a nitrogen atmosphere, 4.3 g (5.4×7.13 mmol) of potassium tert-butoxide is added thereto, and the mixture is stirred for 30 minutes at room temperature. To the above mixture is added a solution of 1.95 g (7.13 mmol) of the aldehyde 7 in 10 ml of dry tetrahydrofuran and the mixture is stirred at room temperature for an hour. The reaction mixture is poured into a mixture of 2N hydrochloric acid and ethyl acetate. After separation, the organic layer is washed with water, dried over magnesium sulfate, and concentrated under reduced pressure to give an oily residue, which is methylated with diazomethane in ethyl ether. The solvent is evaporated and the residue is chromatographed on silica gel. The fractions eluted with n-hexane -ethyl acetate (4:1) are collected to give 946 mg of the desired compound 8a as an oil in 35.7% yield. IR(CHCl$_3$)$\nu$ max: 3460, 1726, 1510, 1015 cm$^{-1}$.

NMR(CDCl$_3$)$\delta$ ppm: 1.16~1.75(m, 8H), 1.79~1.95(m, 2H), 2.03(q, J=7Hz, 2H), 2.28(t, J=7 Hz, 2H), 2.47(br.s, 1H), 3.64(br.s, 4H), 4.97~5.18(m, 1H), 5.05(ABqApartJ=12Hz, 1H), 5.11(ABqBpartJ=12Hz, 1H), 5.23~5.45(m, 2H), 7.35(s, 5H).

(8) Preparation of (1R, 2R, 3S, 4S)-3-benzyloxycarbonylamino-2-[(1Z)-5-(5-tetrazolyl)-1-pentenyl]bicyclo[2.2.1]heptane 8b

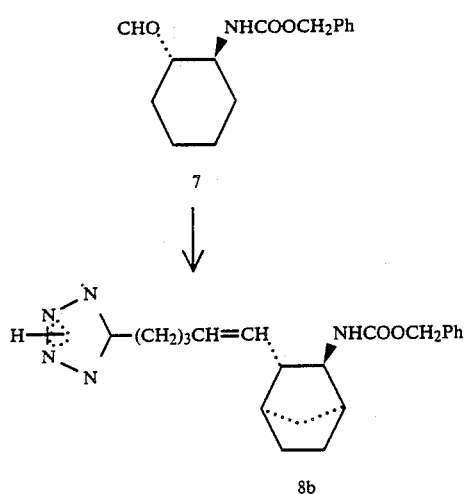

In a nitrogen atmosphere, to a suspension of 11.7 g (3×8.3 mmol) of triphenyl [4-(5-tetrazolyl)butyl]phosphonium bromide [J. Med. Chem., 22, 1340 (1979)] in 110 ml of dry tetrahydrofuran is added 5.0 g (5.4×8.3 mmol) of potassium tert-butoxide and the mixture is stirred at room temperature for 0.5 hours. Under ice-cooling, a solution of 2.28 g (8.3 mmol) of the starting material 7 in 15 ml of dry tetrahydrofuran is added thereto and the mixture is stirred at the same temperature for an hour. The reaction mixture is poured into a mixture of 2N hydrochloric acid and ethyl acetate and separated. The organic layer is washed with water, dried over magnesium sulfate, and concentrated under reduced pressure to give an oily residue which is chromatographed on a silica gel column. The fractions eluted with toluene-ethyl acetate (2:1) mixture are collected to give 1.50 g of crystalline residue which is recrystallized from ethyl ether to give 1.01 g of desired compound 8b in 31.9% yield.

mp. 150°–153° C.

Anal. Calcd. (%) for $C_{21}H_{27}N_5O_2$: C, 66.11; H, 7.13; N, 18.36; Found (%): C, 65.94; H, 7.41; N, 18.14.

$[\alpha]_D$: $-31.3° \pm 0.7°$ (c=0.992, MeOH 24° C.).

IR(CHCl$_3$)$\nu$ max: 3245, 3110, 1672, 1562, 1455, 1301, 1284 cm$^{-1}$.

NMR(CD$_3$OD)$\delta$ ppm: 1.10~1.90(m, 9H), 1.95~2.20(m, 3H), 2.87(t, J=7.9Hz, 2H), 3.46~3.57(m, 1H), 5.01(s, 2H), 5.25~5.48(m, 2H), 7.20~7.44(m, 5H), 7.53~7.74(m, 1H).

EXAMPLE 1

Preparation of (−)-(1R,2R,3S,4S) -methyl (5Z)-6-(3-phenylsulfonylaminobicylco[2.2.1]hept-2-yl)-5-hexenoate Ia-a

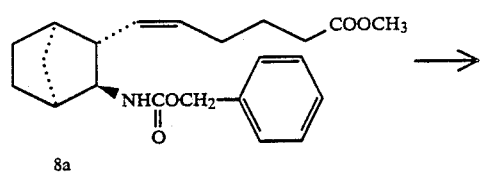

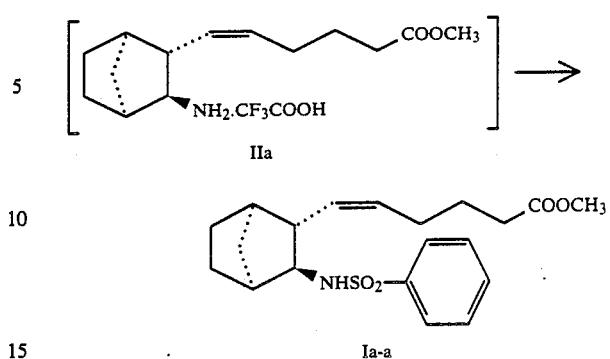

A solution of 2.75 g of the starting material 8a in a mixture of 10 ml of anisole and 30 ml of trifluoroacetic acid is heated for 7 hours at 40° C. The reaction mixture is concentrated under reduced pressure and the residue is rinsed with n-hexane under ice-cooling to give 3.14 g of the trifluoroacetate IIa' in 82.8% purity.

To a solution of the compound IIa' (caluculated to contain to 0.45 g) in 5 ml of dichloromethane are added 0.71 ml of triethylamine and 0.34 g of phenysulfonyl chloride under ice-cooling and the mixture is stirred for 30 minutes at the same temperature. The reaction mixture is partitioned between 2N hydrochloric acid and ethyl acetate. The organic layer is washed with 5% sodium hydrogencarbonate and water successively, dried over magnesium sulfate, and concentrated under reduced pressure. The residue is purified by column chromatography on silica gel and the fractions eluted with n-hexane-ethyl acetate (4:1 to 2:1) are collected to give 0.39 g of the aimed compound in 80.7% yield.

NMR(CDCl$_3$)$\delta$ ppm: 1.17~1.70(m, 8H), 1.80~2.00(m, 4H), 2.19~2.31(m, 1H), 2.25(t, J=7 Hz, 2H), 3.13~3.24(m, 1H), 3.70(s, 3H), 5.08~5.26(m, 3H), 7.41~7.60(m, 3H), 7.70~7.91 (m, 2H).

IR(CHCl$_3$)$\nu$max:3390, 3280, 1730.5, 1162, 1156, 1094 cm$^-$.

$[\alpha]_D$ −69.7±1.1 (c=0.968, MeOH).

Anal. Calcd. (%) for $C_{20}H_{27}NO_4S \cdot 0.01\ C_6H_6$: C, 63.68; H, 7.21; N, 3.70; S, 8.48; Found (%): C, 63.74; H, 7.38; N, 3.76; S, 8.20.

EXAMPLES 2 TO 5

General Procedure for Compound Ib-a to Ie-a

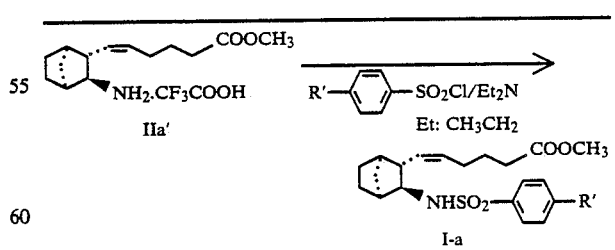

| R' | Compd. No. |
|---|---|
| CH$_3$ | Ib-a |
| OAc | Ic-a |
| Br | Id-a |
| Cl | Ie-a |

EXAMPLE 2

(1R,2R,3S,4S)-methyl (5Z)-6-[3-(p-tolylsulfonylamino)bicyclo[2.2.1]hept-2-yl]-5-hexenoate Ib-a

EXAMPLE 3

(1R,2R,3S,4S)-methyl (5Z)-6-[3-(4-acetoxyphenylsulfonylamino)bicyclo[2.2.1][hept-2-yl]-5-hexenoate Id-a

EXAMPLE 4

(1R,2R,3S,4S)-methyl (5Z)-6[3-(4-bromophenylsulfonylamino)-bicyclo [2.2.1]hept-2-yl]-5-hexenoate Id-a

EXAMPLE 5

(1R,2R,3S,4S)-methyl (5Z)-6[3-(4-chlorophenylsulfonylamino)-bicyclo [2.2.1]hept-2-yl]-5-hexenoate Ie-a To a solution of the compound IIa' (caluculated to contain A [weight]) in B [ml] of dichloromethane are added C [ml] of triethylamine and D [weight] of phenylsulfonyl chloride under ice-cooling and the mixture is stirred for 0.5 to 1 hour at the same temperature. The reaction mixture is partitioned between 2N hydrochloric acid and ethyl acetate. The organic layer is washed with 5% sodium hydrogencarbonate and water successively, dried over magnesium sulfate, and concentrated under reduced pressure. The residue is purified by column chromatography on silica gel and the fractions eluted with n-hexane - ethyl acetate (4:1 to 2:1) are collected to give E [weight] of the aimed compound.

According to the general procedure, the reactions are conducted under the conditions as shown in Table 1 to give the compounds as shown above and shown in Table 2.

TABLE 1

| Ex. No. | A (g) | B (ml) | C (ml) | Chloride R' | D (g) |
|---|---|---|---|---|---|
| 2 | 0.43 | 5 | 0.69 | CH$_3$ | 0.28 |
| 3 | 0.42 | 5 | 0.66 | OAc | 0.29 |
| 4 | 0.50 | 5 | 0.80 | Br | 0.44 |
| 5 | 0.51 | 5 | 0.81 | Cl | 0.37 |

EXAMPLE 6

Preparation of (1R,2R,3S,4S)-(5Z)-6-(3-phenylsulfonylaminobicyclo[2.2.1]hept-2-yl)-5-hexenoic acid Ia-b

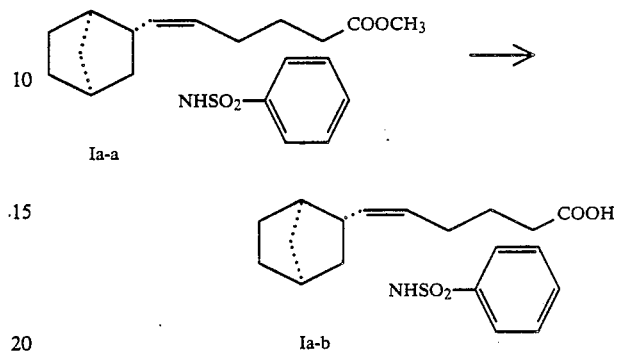

To a solution of 300 ml of the ester Ia-a in 4 ml of methanol is added 1.6 ml of 1N sodium hydroxide in an atmosphere of nitrogen at room temperature and the mixture is allowed to stand for 7 hours at room temperature. The reaction mixture is poured into water and acidified with 2N hydrochloric acid in the presence of ethyl acetate. The organic layer is washed with a saturated aquoues solution of sodium chloride, dried over magnesium suflate, and concentrated under reduced pressure. Benzene is added to the residue and the mixture is concentrated under reduced pressure to give 246 mg of the aimed product as colerless prisms in 85.0% yield.

mp. 107°–109° C.

NMR(CDCl$_3$) δ ppm: 1.14~1.73(m, 8H), 1.80~2.06(m, 4H), 2.19(br. s, 1H), 2.34(t, J=7 Hz, 2H), 3.18(br. s, 1H), 1.10~5.60(br. s, 1H), 5.10~5.26(m, 2H), 5.33~5.50(m, 1H), 7.42~7.61(m, 3H), 7.80~7.92(m, 2H).

[α]$_D$= −77.2°±1.2° (MeOH, c=1.011, 24° C.).

IR(CHCl$_3$) ν max: 3390, 3280, 2965, 2882, 2650br. 1710, 1460, 1449, 1346, 1322, 1311, 1164, 1156, 1096, 1082 cm$^{-1}$. Anal. Calcd. (%) for C$_{19}$H$_{25}$NO$_4$S: C, 62.77; H, 6.95; N, 3.85; S, 8.82; Found (%): C, 62.75; H, 6.86; N, 3.79; S, 8.68.

TABLE 2

| Ex. No. | Compd. no. | E (g) | Yd. (%) | NMR δ ppm (CDCL$_3$) | [α]$_D$ (CH$_3$OH) | IR ν max (CHCL$_3$) [cm$^{-1}$] | Molecular Formula Calcd. (%): Analysis Found (%): |
|---|---|---|---|---|---|---|---|
| 2 | Ib-a | 0.38 | 79.3 | 1.16~1.71 (m, 8H), 1.79 ~2.00 (m, 4H), 2.16~2.29 (m, 1H), 2.26 (t,J = 7Hz, 2H), 2.41 (s, 3H), 3.11~3.21 (m, 1H), 3.69 (s, 3H), 5.02~5.27 (m, 3H), 7.20~7.33 (m, 2H), 7.67~7.80 (m,2H) | −69.0 ± 1.0° (c = 1.008, 23° C.) | 3385, 3275, 1730 1600, 1160, 1093 | C$_{21}$H$_{29}$NO$_4$S C,64.42; H,7.47; N,3.58; S,8.19 C,64.35; H,7.64; N,3.46; S,7.89 |
| 3 | Ic-a | 0.39 | 74.6 | 1.17~1.73 (m, 8H), 1.80~2.03 (m 4H), 2.20~2.40 (m, 1H), 2.26 (t, J = 7Hz, 2H), 2.33 (s, 3H), 3.14~3.27 (m, 1H), 3.70 (s,3H, 5.10~5.27 (m, 3H), 7.17~7.30 (m, 2H), 7.81~7.97n (m, 2H) | −65.0 ± 1.1° (c = 0.939, 23° C.0 | 3390, 3280, 1773 1755, 1730, 1594 1158, 1095 | C$_{22}$H$_{29}$NO$_6$S C,60.67; H,6.71; N,3.22; S,7.36 C,60.88; H,6.69; N,3.10; S,7.09 |
| 4 | Id-a | 0.38 | 70.9 | 1.15~1.73 (m, 8H), 1.82~2.01 (m, 4H), 2.20~2.30 (m, 1H), 2.27 (t, J = 7. OHz, 2H), 3.12~3.24 (m, 1HJ), 3.70 (s, 3H), 5.10~5.27 (m, 3H), 7.55~7.66 (m, 2H), 7.66~7.80 (m, 2H) | −65.3 ± 2.8° (c = 0.383, 23° C.) | 3380, 3280, 2960 2880, 1730, 1578 1438, 1392, 1348 1325, 1165, 1095 1070, 1012 | C$_{29}$H$_{26}$NBrO$_4$S C,52.63; H,5.74; N,3.07; S,7.02 C,52.90; H,5.81; N,3.14; S,6.70 |
| 5 | Ie-a | 0.40 | 80.7 | 1.16~1.76 (m, 8H), 1.83~2.04 (m, 4H), 2.22~2.30 (m, 1H), 2.27 (t, J= 7.OHz, 2H), 3.12~3.24 (m, 1H), 3.70 (s, 3H), 5.08~5.30 (m, 3H), 7.40~7.52 (m, 2H), 7.72~7.88 (m 2H) | −65.4 ± 1.6° (c = 0.662, 23° C.) | 3380, 3280, 2960 2880, 1730, 1590 1480, 1438, 1350 1325, 1165, 1095 1085, 1015 | C$_{20}$H$_{26}$NClO$_4$S C,58.31; H,6.36; N,3.40; Cl,8.61; S,7.78 C,58.50; H,6.34; N,3.53; Cl,8.51; S,7.45 |

EXAMPLES 7 TO 10

General Procedure for Compounds Ib-b to Ie-b

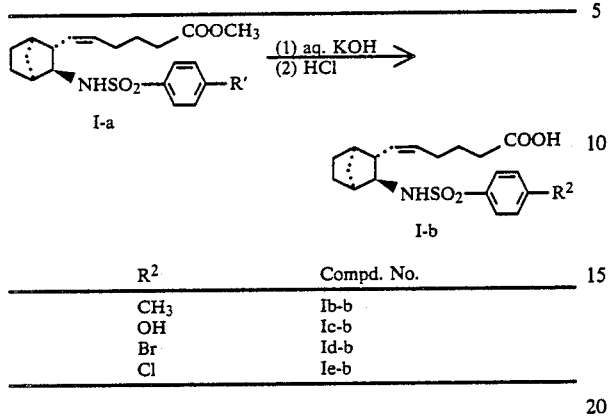

| $R^2$ | Compd. No. |
|---|---|
| $CH_3$ | Ib-b |
| OH | Ic-b |
| Br | Id-b |
| Cl | Ie-b | mixture is allowed to stand for 6 to 7 hours at room temperature. The reaction mixture is poured into water and acidified with 2N hydrochloric acid in the presence of ethyl acetate. The organic layer is washed with a saturated aquoues solution of sodium chloride, dried over magnesium suflate, and concentrated under reduced pressure. Benzene is added to the residue and the mixture is concentrated under reduced pressure to give D [weight] of the aimed carboxylic acid.

According to the general procedure, the reaction is conducted under the conditions as shown in Table 3 to give the compounds above and shown in Table 4.

| Ex. No. | A (mg) | B (ml) | C (ml) |
|---|---|---|---|
| 7 | 330 | 4 | 1.7 |
| 8 | 340 | 6 | 3.1 |
| 9 | 327 | 4 | 1.4 |
| 10 | 345 | 4 | 1.7 |

TABLE 4

| Ex. No. | Compd. No. | D (mg) | Yd. (%) | NMR δ ppm | $[α]_D$ (CH$_3$OH) | IR ν max (CHCl$_3$) [cm$^{-1}$] | Analysis | Molecular Formula Calcd. (%): Found (%): |
|---|---|---|---|---|---|---|---|---|
| 7 | Ib-b | 285 | 86.7 | (CDCl$_3$) 1.13~1.74 (m, 8H), 1.80~2.10 (m, 4H), 2.18 (s,1H), 2.35 (t, = 7 Hz, 2H), 2.41 (s, 3H), 3.10~3.23 (m, 1H), 5.00~5.27 (m, 2H), 5.37 (d, J = 7 Hz, 1H) 7.20~7.33 (m, 2H), 7.66~7.80 (m, 2H) | −65.4 ± 1.1° (c = 0.972, 24° C.) | 3512, 3385, 3270 2640br, 1710, 1601, 1161,1095 | | $C_{20}N_{27}NO_4S.O.12\ C_6H_6$ C,64.21; H,7.22; N,3.62; S,8.28 C,64.00; H,7.31; N,3.35; S,7.87 |
| 8 | Ic-b | 243 | 82.1 | (CD$_3$CN) 1.10~1.64 (m, 8H), 1.74~2.11 (m,5H), 2.24 (t, J = 7.5 Hz, 2H), 2.30~2.90 (br.1H), 3.01~3.10 (m,1H), 5.08~5.22 (m 2H), 5.77 (d, j = 7.5 Hz, 1H), 6.84~6.96 (m,sH), 7.60~7.70 (m, 2H). | −64.1 ± 1.0° (c = 1.023, 24° C.) | 3583, 3382, 3280 1710, 1650 1592, 1501 2600br, 1151, 1095 | | $C_{19}H_{25}NO_5S.O.14\ C_6H_5$ C,61.03; H,6.67; N,3.59; S,8.21 C,6082; H,6.75; N,3.36; S,7.80 |
| 9 | Id-b | 287 | 90.3 | (CDCl$_3$) 1.16~1.80 (m, 8H), 1.80~2.08 (m, 4H), 2.22 (br, s, 1H), 2.36 (t, J = 7.0 Hz, 2H), 3.12~3.25 (m, 1H), 5.06~5.33 (m, 2H), 5.46 (d, J = 7.0 Hz, 1H), 7.57~7.67 (m, 2H), 7.67~7.80 (m, 2H) | −67.8 ± 1.4 (c = 0.793, 23° C.) [mp.116~120° C.] | 3380, 3280, 2960, 2880, 1710, 1578 1392, 1325, 1165, 1152, 1092, 1070 1012 | | $C_{19}H_{24}NBrO_4S.O.2\ C_6H_6$ C, 52.98; H,5.55; N,3.06; S,7.00 C,52.73; H,5.56; N,3.11; S,6.87 |
| 10 | Ie-b | 286 | 85.7 | (CDCl$_3$) 1.15~1.80 (m, 8H), 1.80~2.10 (m, 4H), 2.21 (br, s, 1H), 2.35 (t, J = 7.0 Hz, 2H), 3.10~3.25 (m, 1H), 5.02~5.30 (m, 2H), 5.46 (d, J = 7.0 Hz, 1H), 7.40~7.53 (m, 2H), 7.73~7.88 (m, 2H) | −66.1 ± 2.1 (c = 0.507, 23° C.) | 3380, 3280, 2960, 2880, 1710, 1590, 1480, 1350, 1325, 1165, 1095, 1087 1015 | | $C_{19}H_{24}NClO_4S.O.3\ C_5H_6$ C,59.29; H,6.17; N,3.32; Cl,8.41; S,7.61 C,59.01; H,6.31; N,3.41; Cl,8.33; S,7.42 |

EXAMPLE 7

Preparation of (1R,2R,3S,4S)-(5Z)-6-[3-(p-tolylsulfonylamino)bicyclo[2.2.1]hept-2-yl]-5-hexenoic acid Ib-b

EXAMPLE 8

Preparation of (1R,2R,3S,4S)-(5Z)-6-[3-(4-hydroxyphenylsulfonylamino)bicyclo[2.2.1]hept-2-yl]-5-hexenoic acid Ic-b

EXAMPLE 9

Preparation of (1R,2R,3S,4S)-(5Z)-6-[3-(4-bromophenylsulfonylamino)bicyclo[2.2.1]hept-2-yl]-5-hexenoic acid Id-b

EXAMPLE 10

Preparation of (1R,2R,3S,4S)-(5Z)-6-[3-(4-chlorophenylsulfonylamino)bicyclo[2.2.1]hept-2-yl]-5-hexenoic acid Ie-b To a solution of A [weight] of the ester in B [ml] of methanol is added C [ml] of 1N sodium hydroxide in an atmosphere of nitrogen at room temperature and the

EXAMPLE 11

Preparation of (1R,2R,3S,4S)-sodium (5Z)-6-(3-phenylsulfonylaminobicyclo[2.2.1]hept-2-yl)-5-hexenoate Ia-c

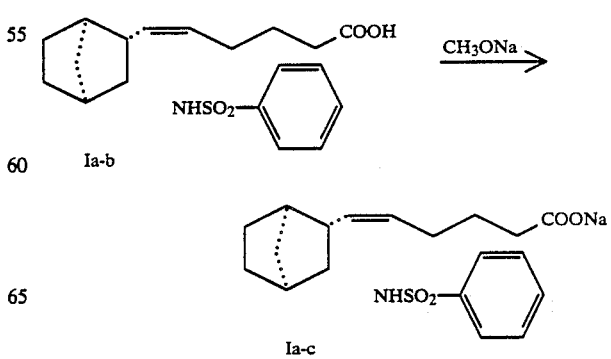

To a solution of 125 mg of the carboxylic acid Ia-b in 2 ml of methanol is added 1.85 ml of 0.177N sodium methoxide in methanol ice-cooling. After two minutes, the mixture is concentrated under reduced pressure. The residue is dissolved in 2 ml of water and the mixture is lyophilized to give 119 mg of the compound Ia-c as a powder in 90.2% yield.

$[\alpha]_D - 70.3° \pm 1.1°$ (MeOH, c=1.013, 23° C.).

IR(KBr) $\nu$ max: 3400, 3290, 3160br. 1565, 1449, 1410, 1320, 1310, 1160, 1097 cm$^{-1}$.

Anal. Calcd. (%) for $C_{19}H_{24}NO_4SNa.0.7H_2O$: C, 57.32; H, 6.44; N, 3.52; S, 8.05; Found (%): C, 57.28; H, 6.17; N, 3.73; S, 8.28.

EXAMPLES 12 TO 15

General Procedure for Compounds Ib-c to Ie-c

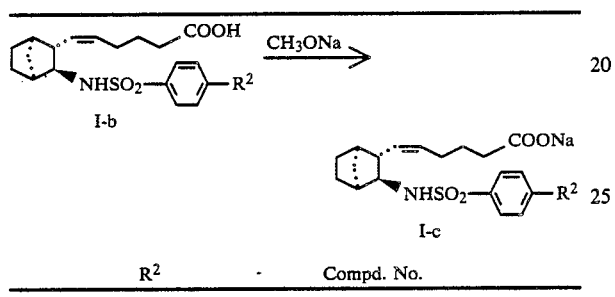

| $R^2$ | Compd. No. |
|---|---|
| $CH_3$ | Ib-c |
| OH | Ic-c |
| Br | Id-c |
| Cl | Ie-c |

EXAMPLE 12

Preparation of (1R,2R,3S,4S)-sodium (5Z)-6-[3-(p-tolylsulfonylamino)bicyclo[2.2.1]hept-2-yl]-5-hexenoate Ib-c

EXAMPLE 13

Preparation of (1R,2R,3S,4S)-sodium (5Z)-6-[3-(4-hydroxyphenylsulfonylamino)bicyclo[2.2.1]hept-2-yl]-5-hexenoate Ic-c

EXAMPLE 14

Preparation of (1R,2R,3S,4S)-sodium (5Z)-6-[3-(4-bromophenylsulfonylamino)bicyclo[2.2.1]hept-2-yl]-5-hexenoate Id-c

EXAMPLE 15

Preparation of (1R,2R,3S,4S)-sodium (5Z)-6-[3-(4-chlorophenylsulfonylamino)bicyclo[2.2.1]hept-2-yl]-5-hexenoate Ie-c To a solution of A [mg] of the carboxylic acid in B [ml] of methanol is added C [ml] of 0.177N sodium methoxide in methanol under ice-cooling. After two minutes, the mixture is concentrated under reduced pressure. The residue is dissolved in 2 ml of water and the mixture is lyophilized to give D [mg] of the aimed compound as a powder.

According to the general procedure, the reaction is conducted under the conditions as shown in Table 5 to give the compounds above and shown in Table 6.

TABLE 5

| Ex. No. | A (ml) | B (ml) | C (ml) |
|---|---|---|---|
| 12 | 236 | 2 | 3.00 |
| 13 | 197 | 2 | 2.64 |
| 14 | 245 | 2 | 2.80 |
| 15 | 238 | 2 | 3.10 |

TABLE 6

| Ex. No. | Compd. No. | D (mg) | Yd. (%) | NMR δ ppm (CD$_3$OD$_3$) | $[\alpha]_D$ (≦ C., CH$_3$OH) | IR $\nu$ max (KBr) [cm$^{-1}$] | Molecular Formula Calcd. (%): Analysis Found (%): |
|---|---|---|---|---|---|---|---|
| 12 | Ib-c | 238 | 99.3 | 1.13~2.23 (m, 13H), 2.10 (t, J = 7.5 Hz, 2H), 2.41 (s, 3H), 3.03~3.14 (m, 1H), 4.96~5.26 (m, 2H), 7.31 (A$_2$B$_2$1-Apart J = 8.4 Hz, 2H), 7.96 (A$_2$B$_2$q-Bpart J = 8.4 Hz, 2H) | −68.9 ± 1.2° (c = 0.917) | 3420, 3260, 3160 1565, 1407, 1320 1156, 1094 | $C_{20}H_{26}NO_4SHa.0.6 H_2O$ C, 58.54; H,6.68; N,3.41; S,7.82 C,58.30; H,6.75; N,3.52; S,8.11 |
| 13 | Ic-c | 192 | 92.0 | 1.10~2.18 (m, 13H), 2.11 (t, j = 7.5 Hz, 2H), 2.97~3.07 (m, 1H), 4.96~5.23 (m, 2H), 6.69~5.79 (m, 2H), 7.50~7.63 (m, 2H) | −70.3 ± 1.1° (c = 1.008) | 3420, 3270, 1630sh, 1564, 1407, 1300, 1147 1092 | $C_{19}H_{24}NO_5SNa.1.1 H_2O$ C,54.16; H,6.27; N,3.33; S,7.61 C,5385; H,6.18; N,3.50; S,7.98 |
| 14 | Id-c | 245 | 96.8 | 1.13~2.23 (m, 13H), 2.10 (t, J = 7.4 Hz, 2H), 3.05~3.16 (m, 1H), 4.95~5.21 (m, 2H), 7.64~7.79 (m, 4H) | −65.7 ± 1.1° (c = 1.000) | 3420, 3280, 3090 2950, 2870, 1570 1407, 1320, 1165 1151, 1092, 1068 1010 | $C_{19}H_{23}NBrNaO_4S.H_2O$ C,47.31; H,5.22; N,2.90; Br,16.57; S,6.65 C,47.46; H,5.01; N,3.08; Br,16.47; S,6.70 |
| 15 | Ie-c | 248 | 98.8 | 1.13~2.22 (m, 13H), 2.08 (t, J = 7.4 Hz, 2H), 3.03~3.14 (m, 1H), 4.92~5.19 (m, 2H), 7.45~7.58 (m, 2H), 7.73~7.86 (m, 2H) | −66.7 ± 1.1° (c = 1.014) | 3420, 3280, 3090 2950, 2870, 1565 1478, 1407, 1320 1160, 1085 | $C_{19}H_{23}NClNaO_4S.1.1 H_2$ C,51.90; H,5.78; N,3.19; Cl,8.06; S,7.29 C,52.11; H,5.70; N,3.23; Cl,7.79; S,7.18 |

EXAMPLE 16

Preparation of (1R,2R,3S,4S)-3-phenylsulfonylamino-2-[(1Z)-5-(5-tetrazolyl)-1-pentenyl]bicyclo[2.2.1]heptane If-b and its sodium salt If-c

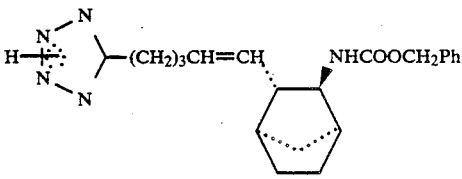

8b

-continued

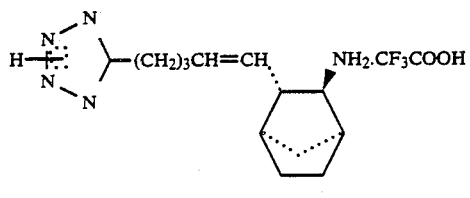

8b'

↓

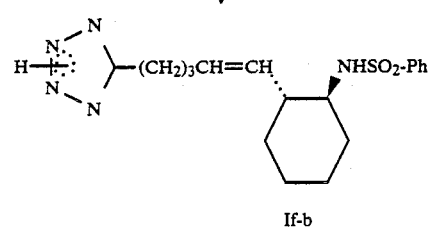

If-b

↓

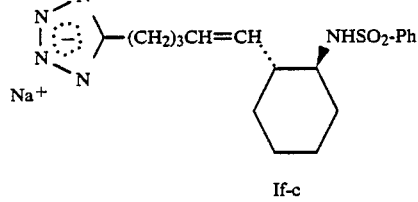

If-c (i) A mixture of 1.03 g of tetrazole 8b in 5 ml of anisole and 20 ml of trifluoroacetic acid is heated at 45° C. for 7 hours. The solvent is evaporated under reduced pressure and the residue is rinsed with n-hexane under ice-cooling to give 1.416 g of gummy substance containing compound 8b' in 68.8% purity from the theory.

To a solution of 452 mg (1.25 mmol) of tetrazole 8b' in a mixture of 4 ml of dichloromethane and 1 ml of dimethylformamide are added 1.0 ml (6×1.25 mmol) of triethylamine and then 0.4 ml (2.5×1.25 mmol) of phenylsulfonyl chloride in a nitrogen atmosphere under ice-cooling and the mixture is stirred at the same temperature for an hour. The reaction mixture is poured into a mixture of 2N hydrochloric acid and ethyl acetate. The organic layer is separated, washed with water, and concentrated under reduced pressure. To a solution of the oily residue in 5 ml of methanol is added 2.5 ml of 1N sodium hydroxide and the mixture is allowed to stand at room temperature for an hour. The reaction mixture is partitioned between water and ethyl ether. The aqeuous layer is acidified with 2N hydrochloric acid in the presence of ethyl acetate. The organic layer is separated, washed with a saturated aqueous solution of sodium chloride, dried over magnesium sulfate, and concentrated under reduced pressure. The residue is chromatographed on silica gel and the fractions eluted with toluene-ethyl acetate (1:1) to ethyl acetate-methanol (10:1) are collected to give 129 mg of the desired compound If-b as a gum in 26.6% yield.

IR(CHCl$_3$) ν max: 3210br, 1670br, 1550, 1155, 1095 cm$^{-1}$.

NMR(CDCl$_3$) δ ppm: 1.10~2.25(m, 13H), 2.94~3.16(m, 2H), 3.23~3.35(m, 1H), 5.15~5.38(m, 2H), 5.69(d, J=7.5), 7.43~7.66(m, 3H), 7.80~7.94(m, 2H).

(ii) To a solution of 114 mg of the starting material If-b in 2 ml of methanol is added 1.58 ml of 0.177 N sodium methoxide under ice-cooling and two minutes later, the mixture is concentrated. The residue is dissolved in 2 ml of water and lyophilized to give 115 mg of the desired If-c as an powder in 97.5% yield.

$[\alpha]_D$ −51.7±1.3° (c=0.692 MeOH 23° C.).

IR(KBr) ν max: 3410br, 1640, 1603, 1448, 1320, 1310, 1160, 1094 cm$^{-1}$.

NMR(CD$_3$OD) δ ppm: 1.13~2.21(m, 13H), 2.73(t, J=7Hz, 2H), 3.10~3.18(m, 1H), 4.98~5.19(m, 2H), 7.38~7.60 (m, 3H), 7.75~7.88(m, 2H).

EXAMPLE 17

Preparation of (1R,2R,3S,4S)-3-(4-bromophenylsulfonylamino)-2-[(1Z)-5-(5-tetrazolyl)pent-1-enyl]bicyclo[2.2.1]heptane Ig-b and its sodium salt Ig-c

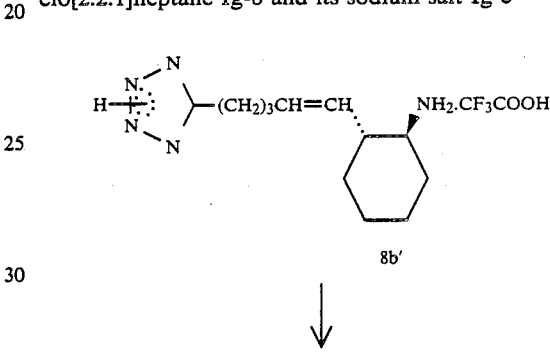

8b'

↓

Ig-b

↓

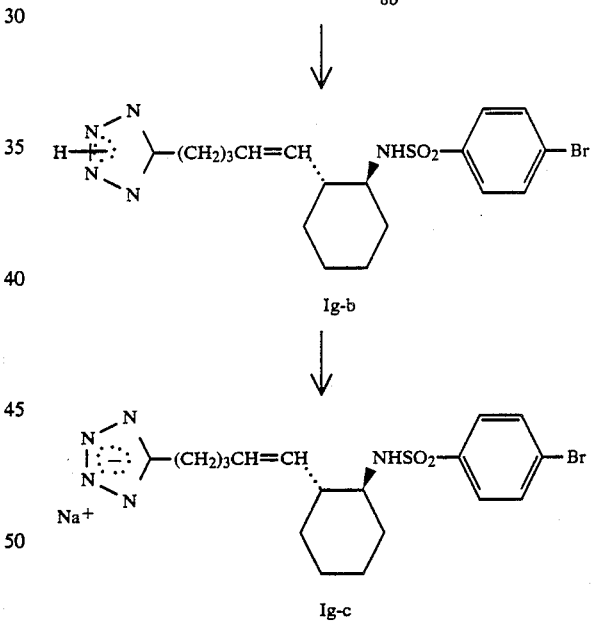

Ig-c

To a solution of 749 mg (1.43 mmol) of the starting material 8b' in a mixture of 4 ml of dichloromethane and 1 ml of dimethylformamide are added 1.19 ml(6×1.43 mmol) of triethylamine and 0.91 g (2.5×1.43 mmol) of 4-bromobenzenesulfonyl chloride in a nitrogen atmosphere under ice-cooling and the mixture is stirred at the same temperature for 1.5 hours. The reaction mixture is poured into a mixture of 2N hydrochloric acid and ethyl acetate. The separated organic layer is washed with a saturated aqueous solution of sodium chloride, dried over magnesium sulfate, and concentrated under reduced pressure to give an oily residue, which is dissolved in 6 ml of methanol. To the resulting solution is added 1N sodium hydroxide and the mixture is allowed to stand at room temperature for 15 minutes. The reaction mixture is poured into water and washed with ethyl ether. The aqueous layer is acidified with 2N hydrochloric acid in the presence of ethyl acetate. After separation, the organic layer is washed with a saturated aqueous solution of sodium chloride, dried over magnesium sulfate, and concentrated under reduced pressure. The residue is chromatographed on a silica gel column and the fractions eluted with toluene-ethyl acetate (1:1) to ethyl acetate-methanol (10:1) are collected to give 330 mg of the aimed compound Ig-b as a gummy residue in 49.5% yield.

Anal. Calcd. (%) for $C_{19}H_{24}N_5BrO_2S.0.32C_6H_6$: C, 51.13; H, 5.32; N, 14.25; S, 6.52; Found (%): C, 50.73; H, 5.41; N, 13.92; S, 6.03.

$[\alpha]_D = -66.6 \pm 1.1°$ (MeOH, c=1.016).

IR(KBr)$\nu$max: 3260(br), 2950, 2880, 1635, 1575, 1555, 1470, 1390, 1322, 1150, 1090, 1068, 1010 cm$^{-1}$.

NMR(CDCl$_3$)$\delta$ ppm: 1.10~2.23(m, 13H), 3.07(t, J=7.0 Hz, 2H), 3.28(br, s, 1H), 5.10~5.40(m, 3H), 6.12(br, s, 1H), 7.55~7.80(m, 4H).

(ii) Compound Ig-b is treated with the same procedure as that of Example 16 to give its sodium salt Ig-c. Anal. Calcd. (%) for $C_{19}H_{23}N_5BrO_2SNa.1.5\ H_2O$: C, 44.28; H, 5.08; N, 13.59; S, 6.22; Found (%): C, 44.73; H, 5.08; N, 13.12; S, 6.64.

$[\alpha]_D = -62.8 \pm 1.0°$ (MeOH, c=1.014).

IR(KBr)$\nu$ max: 3400(br), 2950, 2870, 1640. (br), 1575, 1473, 1390, 1325, 1165, 1092, 1068, 1010 cm$^{-1}$.

NMR(CD$_3$OD)$\delta$ ppm: 1.10~2.04(m, 12H), 2.15(br, s, 1H), 2.73(t, J=7.3Hz, 2H), 3.03~3.16(m, 1H), 4.93~5.20(m, 2H), 7.50~7.76(m, 4H).

The Examples of the pharmacuetical preparation are shown below.

PHARMACUETICAL PREPARATION 1

An injectable solution of thromboxane A$_2$ receptor antagonist for intravenous use in the treatment of thromboxane A$_2$ mediating diseases is produced as follows:

| | |
|---|---|
| (1R,2R,3S,4S)-(5Z)-6-(3-Phenyl-sulfonylaminobicyclo[2.2.1]hept-2-yl-5-hexenoic acid, sodium salt | 625 mg |
| Methyl paraben | 0.5 mg |
| Propyl paraben | 0.1 mg |
| Sodium chloride | 2.5 g |
| Water for injection qs. | 500 ml |

The thromboxane A$_2$ receptor antagonist, preservatives and sodium chloride are dissolved in 300 ml of water for injection and then the volume is brought up to 500 ml. The solution is filtered through a sterile filter and aseptically filled into presterilized vials which are then closed with presterilized rubber closures. Each vial contains a concentration of 25 mg of active ingredient per 20 ml of solution.

PHARMACUETICAL PREPARATION 2

An injectable solution of thromboxane A$_2$ receptor antagonist for intravenous use in the treatment of thromboxane A$_2$ mediating diseases is prepared as described in Pharmacuetical Preparation 1 except that the thromboxane A$_2$ receptor antagonist employed is (1R,2R,3S,4S)-3-phenylsulfonylamino-2-[(1Z)-5-(5-tetrazolyl)-1-pentenyl]bicyclo[2.2.1]heptane, soduim salt.

EXPERIMENT 1

Antagonistic Activity (Inhibitory Effect of Platelets Aggregation on Rat)

Material and Method

From the abdominal artery of a male rat (Sprague-Dowley, 8 weeks old) was collected 10 ml of blood with a plastic syringe containing 1.5 ml of ACD (85 mM of sodium citrate, 70 mM of citric acid, 110 mM of glucose) and 20 $\mu$g of prostaglandin E$_1$. The blood is placed in a plastic test tube, shaken moderately turning and centrifuged for 10 minutes at 160$\times$g to give platelet rich plasma (PRP). To the prepared PRP was added apyrase (25 $\mu$g/ml) and the mixture was layered on 40% bovine serum albumin. The resulting mixture is centrifuged at 1200$\times$g for 25 minutes. The platelet pellets suspended in a small amount of a buffer (137 mM of NaCl, 2.7 mM of KCl, 1.0 mM of MgCl$_2$, 3.8 mM of NaH$_2$PO$_4$, 3.8 mM of Hepes, 5.6 mM of glucose, 0.035% of bovine serum albumin, pH 7.35) was applied on 10 ml of Sephaose 2B column and eluted with such a buffer to prepare washed platelets.

The platelet aggregation reaction was measured by an aggregometer (NKK HEMA TRACER 1 MODEL PAT-6A.6M, Niko bioscience). In a measuring cuvette was placed 245 $\mu$l of the washed platelets of which platelet concentration was adjusted to 5$\times$10$^5$/ $\mu$l and set in the aggregometer. The adjusted washed platelet was stirred (1000 rpm) at 37° C. and 3.8 $\mu$l of 0.1M of CaCl$_2$ was added thereto. One minute later, 0.5 $\mu$l of a solution of a test compound in dimethylsulfoxide was added and 2 minutes later, 1 $\mu$l of collagen (Collagen reagent Horm®, HORMON-CHEMIE München GMBH, final concentration 4 $\mu$g/ml) as an inducer for platelet aggregation was added. The platelet aggregation was monitored with an aggregometer in terms of the increase and decrease in light transmission.

Concentration of 50% inhibition was calculated from the inhibitory rate of aggregation (this correspondes to light transmission of a sample which is measured at 3 minutes after the addition of a platelet aggregating inducer, provided that light transmissions of the washed platelets and the buffer samples are taken as 0% and 100%, respectively.)

The results of the test are shown in Table 7.

EXPERIMENT 2

Partial Agonistic Activity (Shape Change of Rat Platelets)

Material and Method

The measurement of partial agonistic activity was carried out according to the method shown for platelet aggregation. To the washed platelets was added 0.1M of CaCl$_2$ and one minute later a test compound was added thereto. The decrease in light transmission caused by the test compound itself was measured to estimate the activity. As a standard, the maximal agonistic activity of the reference compound was taken as 100% and the concentration of the test compound which showed the 50% activity to that of the standard was indicated as ED$_{50}$.

TABLE 7

| Compd. No.* | Inhibition for Platelet Aggregation IC$_{50}$ | Activity of Partial Agonist EC$_{50}$ |
| --- | --- | --- |
| Ia-c | 6 nM | >1000 nM |
| Ib-c | 6 nM | >1000 nM |
| Ic-c | 6 nM | 150 nM |
| Id-c | 5 nM | 130 nM |
| Ie-c | 5 nM | 300 nM |
| If-c | 4 nM | >1000 nM |
| Rf. Compd. | 2 nM | 1 nM |

*The number corresponds to the one used in the examples. The reference compound is shown below.

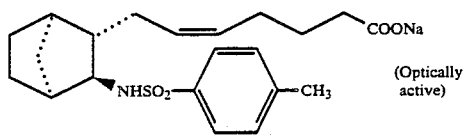

(Optically active)

The compound which seems to have the most potent inhibitory activity for platelet aggregation is elected as the reference compound, the racemate of which is disclosed in the U.S. Pat. No. 4,861,913 (I-1 Example 16; Table 1).

As clearly shown by the results, the compounds of the invention have the comparable activity for the main effect to the conventional thromboxane A$_2$ receptor antagonist, and, moreover, the partial agonistic activity of the compounds of this invention is only about 1/130 time or less than that of reference compound.

The respiratory inhibition action which occurred when TXA$_2$ receptor antagonist was intravenously injected to mice was examined as an index of partial agonistic activiy (in vivo). As a result of the examination, it was confirmed that the compounds of this invention showed only the extremely low partial agonistic activity in comparison with the corresponding heptenoic acid derivatives.

Acute Toxicity 1

Material and Method

Male Scl-ddY mice (4-week-age, 23–27 g) were used. Each experimental group consists of 5 animals. After injecting the test compound dissolved in saline into a tial vein, the mortality within 24 hours was obtained as an LD$_{50}$ value by the Probit method. The results were shown in Table 8.

TABLE 8

| Compd. No. | LD$_{50}$ [mg/Kg] |
| --- | --- |
| Ia-c | 237.0 |
| If-c | 209.4 |

What we claim is:

1. A compound of the formula

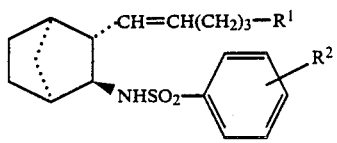

wherein $R^1$ is carboxyl, $R^2$ is hydrogen, methyl, hydroxy, chloro or bromo; or a therapeutically acceptable ester of salt thereof.

2. A compound as claimed in claim 1 wherein the said compound is (1R,2R ,3S,4S)-(5Z)-6-(3-phenylsulfonylaminobicyclo[2.2.1]heptyl)-5-hexenoic acid.

3. A pharmaceutical preparation for injectable use in the treatment of thromboxane A$_2$ mediating diseases in mammals, comprising a therapeutically effective amount of at least one compound of the formula:

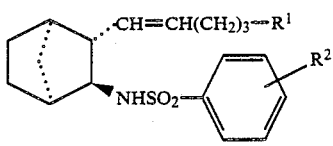

wherein $R^1$ is carboxy; $R^2$ is hydrogen, methyl, hydroxy, chloro or bromo; or a therapeutically acceptable ester or salt thereof, together with at least one non-toxic therapeutically acceptable carrier.

4. A pharmaceutical preparation claimed in claim 3 wherein the said compound is (1R,2,3S,4S)-(5Z) -6-(3-phenylsulfonylaminobicyclo[2.2.1]heptyl)-5-hexenoic acid.

5. A method for treating thromboxane A$_2$ mediating diseases in mammals, comprising administering intravenously to mammals in need of such treatment a therapeutically effective amount of a compound of the formula:

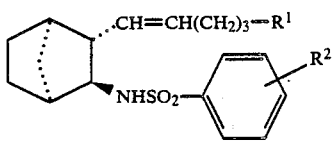

wherein $R^1$ is carboxyl; $R^2$ is hydrogen, methyl, hydroxy, chloro, or bromo; or a therapeutically acceptable ester or salt thereof, together with at least one non-toxic therapeutically acceptable carrier.

6. A method claimed in claim 5 wherein the said compound is (1R,2R,3S,4S) -(5Z)-6-(3-phenylsulfonylaminobicyclo-[2.2.1]heptyl-5-hexenoic acid.

* * * * *